United States Patent
Shikata et al.

(10) Patent No.: US 10,267,814 B2
(45) Date of Patent: Apr. 23, 2019

(54) REAGENT PREPARATION SUPPORT EQUIPMENT, PROGRAM FOR IMPLEMENTATION THEREOF, AND COMPUTER-READABLE RECORDING MEDIUM ON WHICH THIS PROGRAM IS RECORDED

(71) Applicant: SHIMADZU CORPORATION, Kyoto-shi, Kyoto (JP)

(72) Inventors: Masamitsu Shikata, Nakagyo-ku (JP); Nobuyuki Akinaga, Nakagyo-ku (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/396,888

(22) PCT Filed: Feb. 1, 2013

(86) PCT No.: PCT/JP2013/052392
§ 371 (c)(1),
(2) Date: Sep. 18, 2015

(87) PCT Pub. No.: WO2013/168441
PCT Pub. Date: Nov. 14, 2013

(65) Prior Publication Data
US 2016/0187360 A1 Jun. 30, 2016

(30) Foreign Application Priority Data
May 11, 2012 (JP) ................. 2012-109249

(51) Int. Cl.
*G01N 35/00* (2006.01)
*B01L 9/06* (2006.01)

(52) U.S. Cl.
CPC .......... *G01N 35/00663* (2013.01); *B01L 9/06* (2013.01); *G01N 35/00584* (2013.01);
(Continued)

(58) Field of Classification Search
CPC ... G01N 35/00663; G01N 2035/00673; G01N 2035/00891; G01N 2035/0091
See application file for complete search history.

(56) References Cited

U.S. PATENT DOCUMENTS

| 6,058,764 A | 5/2000 | Yamada et al. |
| 2010/0115463 A1* | 5/2010 | Kondou ............... B01L 3/527 715/803 |
| 2011/0245089 A1* | 10/2011 | Scott ..................... G06F 19/366 506/7 |

FOREIGN PATENT DOCUMENTS

| JP | 61-204565 A | 9/1986 |
| JP | 05-164760 A | 6/1993 |
| JP | 11-072498 A | 3/1999 |

OTHER PUBLICATIONS

English translation of International Search Report (Form PCT/ISA/210) of International Application No. PCT/JP2013/052392 dated Apr. 9, 2013 (1 page).
(Continued)

*Primary Examiner* — Kathryn Wright
(74) *Attorney, Agent, or Firm* — Westerman, Hattori, Daniels & Adrian

(57) ABSTRACT

Disclosed herein is a reagent preparation supporting device including: reagent kit information storing means that stores amounts of reagents required for one analysis and a composition of a reaction liquid to be prepared; an input unit that inputs the number of samples to be analyzed; reagent amount calculating means that calls up, from the reagent kit information storing means, the data regarding the reagent kit to calculate required amounts of the reagents included in the reagent kit and a composition of the reaction liquid according to the number of samples inputted through the input unit; and a display unit that displays, as a reagent preparation table, the required amounts of the reagents included in the
(Continued)

reagent kit and the composition of the reaction liquid to be prepared based on results calculated by the reagent amount calculating means.

8 Claims, 8 Drawing Sheets

(52) U.S. Cl.
CPC .. *G01N 35/00722* (2013.01); *B01L 2200/023* (2013.01); *B01L 2200/16* (2013.01); *G01N 2035/0091* (2013.01); *G01N 2035/00673* (2013.01); *G01N 2035/00891* (2013.01)

(56) References Cited

OTHER PUBLICATIONS

English translation of International Preliminary Report on Patentability (Form PCT/IB/373) of International Application PCT/JP2013/052392 dated Nov. 11, 2014 with Form PCT/ISA/237 (5 pages).

\* cited by examiner

REAGENT PREPARATION SUPPORT EQUIPMENT, PROGRAM FOR IMPLEMENTATION THEREOF, AND COMPUTER-READABLE RECORDING MEDIUM ON WHICH THIS PROGRAM IS RECORDED

TECHNICAL FIELD

The present invention relates to a device for supporting the operation of preparing reaction liquids from reagent kits for use in various analyses in the fields of life science, medicine, agriculture, chemistry, or forensic medicine, a program for implementing the same, and a computer-readable recording medium on which the program is recorded.

BACKGROUND ART

A reagent kit includes reagents required for analysis of a sample, and also prescribes a procedure for preparing these reagents. Examples of such analysis include: detection of a specific sequence or a gene mutation, such as SNP (Single Nucleotide Polymorphism), present in genomic DNA or RNA of animals including humans, plants, bacteria, or viruses with the use of a gene analyzer; detection of presence or absence of a protein; and enzymatic reaction. The present invention can be applied not only to these analyses but also to all the analyses using a reagent kit.

In the field of life science such as in research on gene analysis or clinical examination, various reagent kits are provided. Many reagent kits are designed to be used for analysis by mixing two or more reagents included therein to prepare a reaction liquid and then mixing the reaction liquid with a sample to be analyzed. The amounts of the individual reagents to be mixed to prepare a reaction liquid are specified in their instruction manuals.

In many cases, only the amounts of the reagents required to be prepared for analysis of one sample are described in the instruction manuals. Therefore, each time analysis needs to be performed, an operator (reagent kit user) prepares reaction liquids one by one according to the number of samples, or prepares a reaction liquid in an amount corresponding to the number of samples at a time and then dispenses the reaction liquid into the individual samples. However, the amount of a reaction liquid required for analysis of one sample is several tens of microliters or less, and therefore, in the former case where a reaction liquid is prepared for each sample in such a small amount, it is difficult to uniformly prepare all the reaction liquids, which is one of the causes of variations in results. Therefore, many reagent kit operators prepare a reaction liquid in an amount corresponding to the number of samples at a time, and then dispense the reaction liquid into the individual samples.

SUMMARY OF THE INVENTION

Problems to be Solved by the Invention

Even in the case of analysis of one sample, a reaction liquid needs to be prepared in an amount required for three reactions to perform analysis of a sample itself and analysis of positive and negative controls for verification of the correctness of reaction. When reagents are each prepared in an amount corresponding to the number of samples at a time to prepare a reaction liquid for analysis of two or more reactions, the amounts of the reagents to be contained in the reaction liquid need to be calculated for each analysis before the reagents are injected into a tube (reaction vessel) to prepare the reaction liquid. Such calculations of the amounts of the reagents are performed using a desk calculator or a spreadsheet. Therefore, in addition to a problem that the calculations are troublesome, performing the calculations for each analysis increases the risk of miscalculation and also causes an error in preparing the reaction liquid.

It is therefore an object of the present invention to solve such problems associated with calculations of the amounts of reagents that need to be performed by a human, such as a reagent kit operator, to prepare a reaction liquid.

Means for Solving the Problems

The present invention provides: a reagent preparation supporting device, in which the required amounts of reagents included in a reagent kit used and the composition of a reaction liquid to be prepared are automatically displayed as a reagent preparation table, preferably a preparation procedure is further automatically displayed, by inputting the number of samples to be analyzed so that an operator can prepare a reaction liquid simply by injecting the displayed amounts of individual reagents into a tube based on the displayed reagent preparation table or preparation procedure; a program for implementing the same; and a computer-readable recording medium on which the program is recorded.

The present invention is directed to a reagent preparation supporting device comprising: reagent kit information storing means that stores, as data, amounts of reagents required for one analysis using a reagent kit for sample analysis and a composition of a reaction liquid to be prepared; an input unit that inputs number of samples to be analyzed; reagent amount calculating means that calls up the data regarding the reagent kit from the reagent kit information storing means to calculate required amounts of the reagents included in the reagent kit and a composition of the reaction liquid according to the number of samples inputted through the input unit; and a display unit that displays, as a reagent preparation table, the required amounts of the reagents included in the reagent kit and the composition of the reaction liquid to be prepared based on results calculated by the reagent amount calculating means.

It is preferred that the reagent kit information storing means stores data regarding two or more kinds of reagent kits, the input unit is configured to designate any one of the two or more kinds of reagent kits data of which is stored in the reagent kit information storing means, and the reagent amount calculating means calls up, from the reagent kit information storing means, the data regarding the reagent kit designated through the input unit to calculate required amounts of the reagents and a composition of the reaction liquid. The designation of a reagent kit to be used through the input unit can be performed by direct input through a keyboard or a bar code reader. However, the two or more kinds of reagent kits data of which is stored in the reagent kit information storing means are preferably displayed on the display unit so that a reagent kit to be used can be selected from them, which makes it easy to designate a reagent kit to be used.

The reagent kit information storing means previously stores information regarding commercially-available reagent kits to which this supporting device can be applied. Further, it is also preferred that the reagent kit information storing means is constituted from a recordable storage unit so that data regarding a new reagent kit can be added thereto. When the reagent kit information storing means has such a structure, a reagent preparation table for a new reagent kit can also be created and displayed on the display unit by adding information regarding the new reagent kit, to which this supporting device has become applicable, to the reagent kit information storing means.

Further, it is preferred that the reagent preparation supporting device includes reaction liquid information storing means that is capable of storing the results calculated by the reagent amount calculating means and calling up the results at any time to display the results on the display unit. The reaction liquid information storing means records the result of preparation of the reaction liquid used, and therefore, after the measurement of a sample, the presence or absence of an error in preparing the reaction liquid can be verified based on the measurement result of the sample.

Further, it is preferred that the display unit is configured to also display tubes and the reagents, the sample, or the reaction liquid to be dispensed into the individual tubes. This makes it possible for an operator to easily prepare reaction solutions to be analyzed without an error by dispensing the sample and the prepared reaction liquid into the individual tubes displayed on the display unit.

Further, it is preferred that a rack for placing tubes for reagent preparation is provided to easily perform a reagent preparation operation. In order to easily perform a preparation operation using the rack, the reagent preparation supporting device further includes: rack screen storing means that stores image data of a rack screen showing positions of holes for placing tubes for reagent preparation in the rack; and display control means that allows the display unit to display the rack screen stored in the rack screen storing means, to show, on the displayed rack screen, positions of holes for placing tubes for reagent preparation required to prepare the reagents according to the reagent preparation table, and to also display a procedure for preparing the reagents based on the reagent preparation table. In this case, it is more preferred that the display control means allows the display unit to also display injection amounts of the reagents in addition to the procedure for preparing the reagents based on the reagent preparation table. This makes it possible for an operator to prevent a preparation error by placing tubes for reagent preparation in their corresponding positions in the rack according to the positions of holes for placing tubes for reagent preparation shown on the rack screen displayed on the display unit and by performing a preparation operation according to the preparation procedure displayed on the display unit.

Further, when receiving an external signal relating to a reagent preparation operation, the display control means changes display on the rack screen showing positions of holes for placing tubes for reagent preparation and displayed on the display unit according to the reagent preparation procedure. The external signal relating to a reagent preparation operation is, for example, a signal from input means, such as a foot switch, connected to a computer implementing the reagent preparation supporting device, and can be inputted each time one step of the preparation operation performed by an operator is finished. Displaying the finished step of the preparation operation on the display screen in this way makes it possible to further prevent the occurrence of a preparation error.

The present invention includes not only a reagent preparation supporting device implemented as an dedicated device but also a CPU for controlling an analyzer or a general-purpose computer, such as a personal computer, that is allowed to function as a reagent preparation supporting device by installing a program developed by software on the CPU or the computer. The present invention also includes a program developed by software for such a purpose.

The present invention is also directed to a program developed by software for allowing a computer to function as a reagent preparation supporting device, a reagent preparation supporting program allowing a computer to function as: reagent kit information storing means that stores, as data, amounts of reagents required for one analysis using a reagent kit for sample analysis and a composition of a reaction liquid to be prepared; an input unit that performs input of the number of samples to be analyzed; reagent amount calculating means that calls up the data regarding the reagent kit from the reagent kit information storing means to calculate required amounts of the reagents included in the reagent kit and a composition of the reaction liquid according to the number of samples inputted through the input unit; and a display unit that displays, as a reagent preparation table, the required amounts of the reagents included in the reagent kit and the composition of the reaction liquid to be prepared based on results calculated by the reagent amount calculating means.

It is preferred that in the program, the reagent kit information storing means stores data regarding two or more kinds of reagent kits, the input unit is configured to designate any one of the two or more kinds of reagent kits data of which is stored in the reagent kit information storing means, the reagent amount calculating means calls up, from the reagent kit information storing means, the data regarding the reagent kit designated through the input unit to calculate required amounts of the reagents and a composition of the reaction liquid.

Further, it is preferred that the program allows the computer to further function as reaction liquid information storing means that is capable of storing the results calculated by the reagent amount calculating means and calling up the results at any time to display the results on the display unit.

Further, it is preferred that the program allows the display unit to also display tubes for reagent preparation and the reagents, the sample, or the reaction liquid to be dispensed into the individual tubes.

Further, it is preferred that a rack for placing tubes for reagent preparation is provided. In this case, it is preferred that the program further allows the computer to function as: rack screen storing means that stores image data of a rack screen showing positions of holes for placing tubes for reagent preparation in the rack; and display control means that allows the display unit to display the rack screen stored in the rack screen storing means, to show, on the displayed rack screen, positions of holes for placing tubes for reagent preparation required to prepare the reagents according to the reagent preparation table, and to also display a procedure for preparing the reagents based on the reagent preparation table. It is further preferred that the display control means allows the display unit to also display injection amounts of the reagents in addition to the procedure for preparing the reagents based on the reagent preparation table.

In the case of the program that allows the display unit to display a rack screen in the rack, when receiving an external signal relating to a reagent preparation operation, the display control means preferably changes display on the rack screen showing positions of holes for placing tubes for reagent preparation and displayed on the display unit according to the reagent preparation procedure.

The present invention is also directed to a computer-readable recording medium on which the reagent preparation supporting program according to the present invention is recorded. Examples of such a recording medium include CDs, USB memories, and SD cards.

The program according to the present invention is not limited to one recorded on such a recording medium, and can be provided by downloading from the Internet.

Effects of the Invention

According to the present invention, the amounts of reagents to be prepared according to the number of samples to be analyzed can be calculated simply by inputting the number of samples into a computer. Therefore, an operator does not need to perform such troublesome calculations. Further, the operator can prepare a reaction liquid simply by injecting, into a tube, the reagents in amounts shown in the reagent preparation table displayed on the display unit, which makes it possible to reduce the risk of an error in reagent preparation.

EMBODIMENTS OF THE INVENTION

Figure 1:
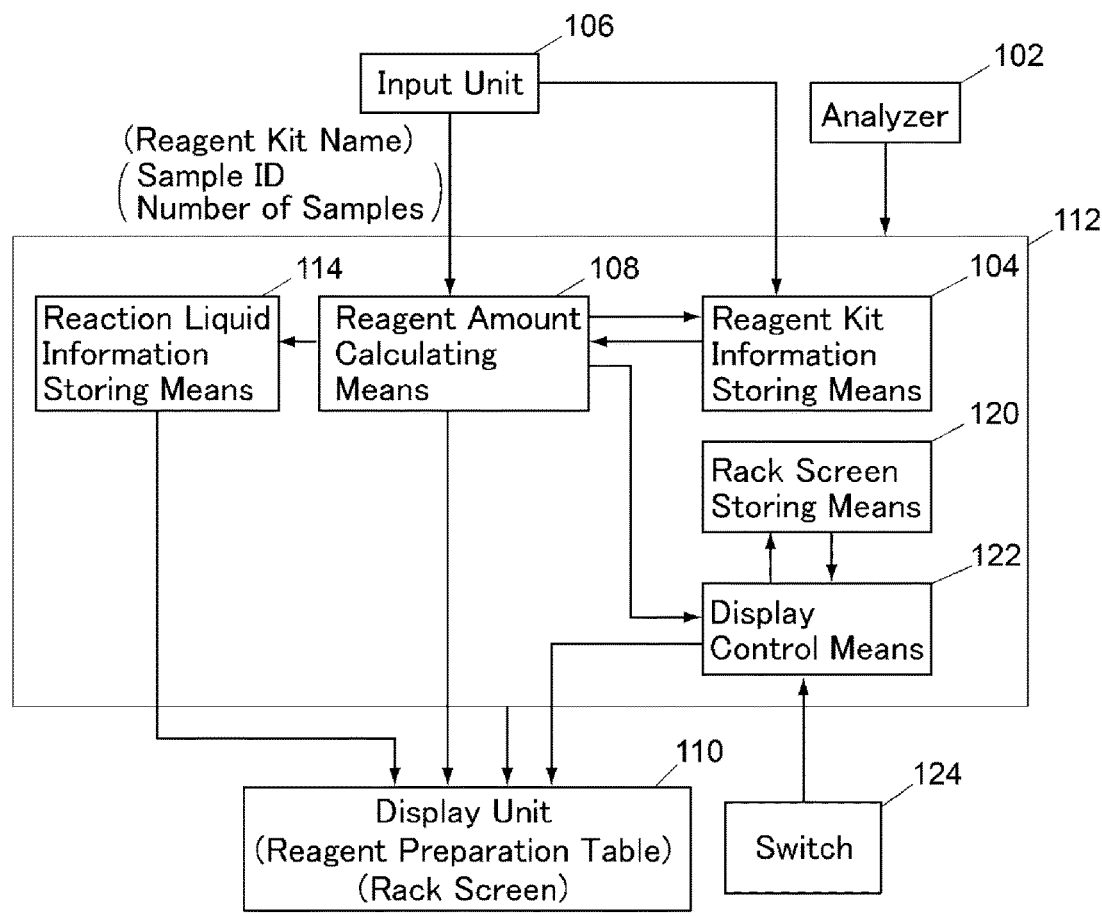
FIG. 1 is a block diagram of one embodiment of the present invention.

First, a procedure for preparing a reaction liquid will be described with reference to a case where a certain reagent kit is used. This reagent kit includes six kinds of reagents; a reagent A, a reagent B, a reagent C, a reagent D, a reagent E-1, and a reagent E-2. These reagents are used to prepare two kinds of reaction liquids, R1 and R2, and then these two kinds of reaction liquids are dispensed into identical samples, respectively, to cause a reaction to obtain one analytical result. The reaction liquids R1 and R2 are prepared so as to contain a common mixed liquid of the reagents A, B, C, and D, and are therefore the same in reagent A, B, C, and D contents and the mixing ratio among the reagents A, B, C, and D. The reaction liquid R1 is prepared by adding the reagent E-1 to the common mixed liquid, and the reaction liquid R2 is prepared by adding the reagent E-2 to the common mixed liquid.

Table 1 is a reagent preparation table for one analysis, which is specified in the specifications of this reagent kit. In the present invention, the amounts of the individual reagents required for one analysis and the compositions of the reaction liquids R1 and R2 to be prepared shown in Table 1 are stored in reagent kit information storing means.

TABLE 1

| Reagent name | Required amount for one analysis |
|---|---|
| Preparation 1 - Common mixed liquid | |
| Reagent A | 25 µL |
| Reagent B | 10 µL |
| Reagent C | 10 µL |
| Reagent D | 5 µL |
| Preparation 2 - Reaction liquid R1 | |
| Common mixed liquid | 25 µL |
| Reagent E-1 | 15 µL |
| Sample | 10 µL |
| Preparation 3 - Reaction liquid R2 | |
| Common mixed liquid | 25 µL |
| Reagent E-2 | 15 µL |
| Sample | 10 µL |

When analysis is performed using this reagent kit, positive and negative control reactions need to be performed in addition to the reaction with the sample. Therefore, when the number of samples is 1, each of the reaction liquids R1 and R2 needs to be prepared in an amount required for three reactions to perform a positive control reaction, a negative control reaction, and a reaction with one sample. Similarly, when the number of samples is 5, each of the reaction liquids R1 and R2 needs to be prepared in an amount required for seven reactions to perform a positive control reaction, a negative control reaction, and reactions with five samples.

Table 2 shows the amounts of the reagents required to be prepared to perform analysis of one sample or analyses of five samples and positive and negative control reactions.

TABLE 2

| Reagent name | One sample | Five samples |
|---|---|---|
| Preparation 1 - Common mixed liquid | | |
| Reagent A | 75 µL | 175 µL |
| Reagent B | 30 µL | 70 µL |
| Reagent C | 30 µL | 70 µL |
| Reagent D | 15 µL | 35 µL |
| Preparation 2 - Reaction liquid R1 | | |
| Common mixed liquid | 75 µL | 175 µL |
| Reagent E-1 | 45 µL | 105 µL |
| | 40 µL × 3 reactions | 40 µL × 7 reactions |
| Preparation 3 - Reaction liquid R2 | | |
| Common mixed liquid | 75 µL | 175 µL |
| Reagent E-2 | 45 µL | 105 µL |
| | 40 µL × 3 reactions | 40 µL × 7 reactions |

The amounts of the reagents in the reagent preparation table shown in Table 2 are conventionally calculated manually. However, in the present invention, the amounts of the reagents are automatically calculated by reagent amount calculating means 108 to be described later with reference to FIG. 1, and are automatically displayed as a reagent preparation table such as Table 2 by a display unit.

Hereinafter, an embodiment of the present invention will be described.

FIG. 1 is a block diagram showing one example of the embodiment together with an analyzer. A reagent preparation supporting device of this example is implemented as an attachment device of an analyzer 102. Examples of the analyzer 102 include various analyzers for use in the fields of life science, medicine, agriculture, chemistry, or forensic medicine. One example of the analyzer 102 is a gene analyzer that performs detection of genetic polymorphism etc.

Reagent kit information storing means 104 is a storage unit of a computer, and stores, as data, the amounts of reagents required for one analysis using a reagent kit for sample analysis and the composition of a reaction liquid to be prepared. The data stored in the reagent kit information storing means 104 is, for example, data shown in Table 1. The reagent kit information storing means 104 is constituted from, for example, a non-volatile semiconductor storage unit such as an EPROM or an EEPROM or a disk memory.

An input unit 106 is intended to perform input of the number of samples to be analyzed, and examples of the input unit 106 include a keyboard and a bar code reader. When the reagent kit information storing means 104 stores information regarding two or more kinds of reagent kits, the input unit 106 is also used to designate a reagent kit to be used. The input unit 106 may be one that makes it possible to interactively input information with the aid of a display unit 110 connected as a display device to the computer. The input unit 106 is not limited to a single device, and may be a combination of two or more kinds of input devices including a keyboard, a display device, and a bar code reader.

Reagent amount calculating means 108 calls up the data regarding the reagent kit from the reagent kit information storing means 104, and calculates the required amounts of the reagents included in the reagent kit and the composition of the reaction liquid according to the number of samples inputted through the input unit 106. When the reagent kit information storing means 104 stores information regarding two or more kinds of reagent kits, the data regarding the reagent kit called up from the reagent kit information storing means 104 is data regarding the reagent kit designated through the input unit 106.

The reagent amount calculating means 108 is a function implemented by software installed on the computer 112. When this reagent preparation supporting device is implemented as a dedicated device, the computer 112 is a CPU of the reagent preparation supporting device or a computer such as a microcomputer system. On the other hand, when not being a dedicated device, this reagent preparation supporting device may be implemented by a computer of another device or a general-purpose computer by installing a program developed by software thereon. Such a computer used when the reagent preparation supporting device is not a dedicated device is, for example, a data processing computer, such as a CPU, for performing operations or data processing of the analyzer 102 or a general-purpose personal computer.

The display unit 110 displays, as a reagent preparation table, the required amounts of the reagents included in the reagent kit and the composition of the reaction liquid to be prepared based on results calculated by the reagent amount calculating means 108. The display unit 110 is a display device, such as a liquid crystal display device, connected to the computer 112.

In this example, the reagent kit information storing means 104 stores data regarding two or more kinds of reagent kits so that the reagent preparation supporting device can be used for two or more kinds of reagent kits. The input unit 106 is configured not only to input the number of samples but also to designate any one of the two or more kinds of reagent kits data of which is stored in the reagent kit information storing means 104. The input unit 106 is configured to allow the display unit 110 to display the names of the two or more kinds of reagent kits data of which is stored in the reagent kit information storing means 104. In this case, one example of such an input unit 106 includes the display unit 110 that displays the names of the two or more kinds of reagent kits data of which is stored in the reagent kit information storing means 104 and a keyboard or a mouse for selecting one of the two or more kinds of reagent kits displayed on the display unit 110 to designate it as a reagent kit to be used.

Further, in this example, the reagent kit information storing means 104 is recordable such as a non-volatile semiconductor storage unit such as an EPROM or an EEPROM or a disk memory so that data regarding a new reagent kit can be added by inputting the data through the input unit such as a bar code reader or a keyboard.

Further, in this example, the computer 112 includes reaction liquid information storing means 114 that is capable of storing the results calculated by the reagent amount calculating means 108 and calling up the results at any time to display the results on the display unit 110. The reaction liquid information storing means 114 is configured to record information regarding reaction liquids prepared in the past such as the reagent preparation table of a prepared reaction liquid, requested date and time of preparation of the reaction liquid, sample ID, reagent kit name, operator ID, and operator name so that such information can be displayed on the display unit 110 at any time by the instruction from the input unit 106. The reaction liquid information storing means 114 is also constituted from, for example, a non-volatile semiconductor storage unit such as an EPROM or an EEPROM or a disk memory.

Hereinafter, referring to FIGS. 2A, 2B, 3, 4, and 5, the operation of preparing reaction liquids from a certain reagent kit with the use of the reagent preparation supporting device of an example will be described. In this case, the operation will be described with reference to a case where SNP is detected by performing a gene amplification reaction.

Figure 3:
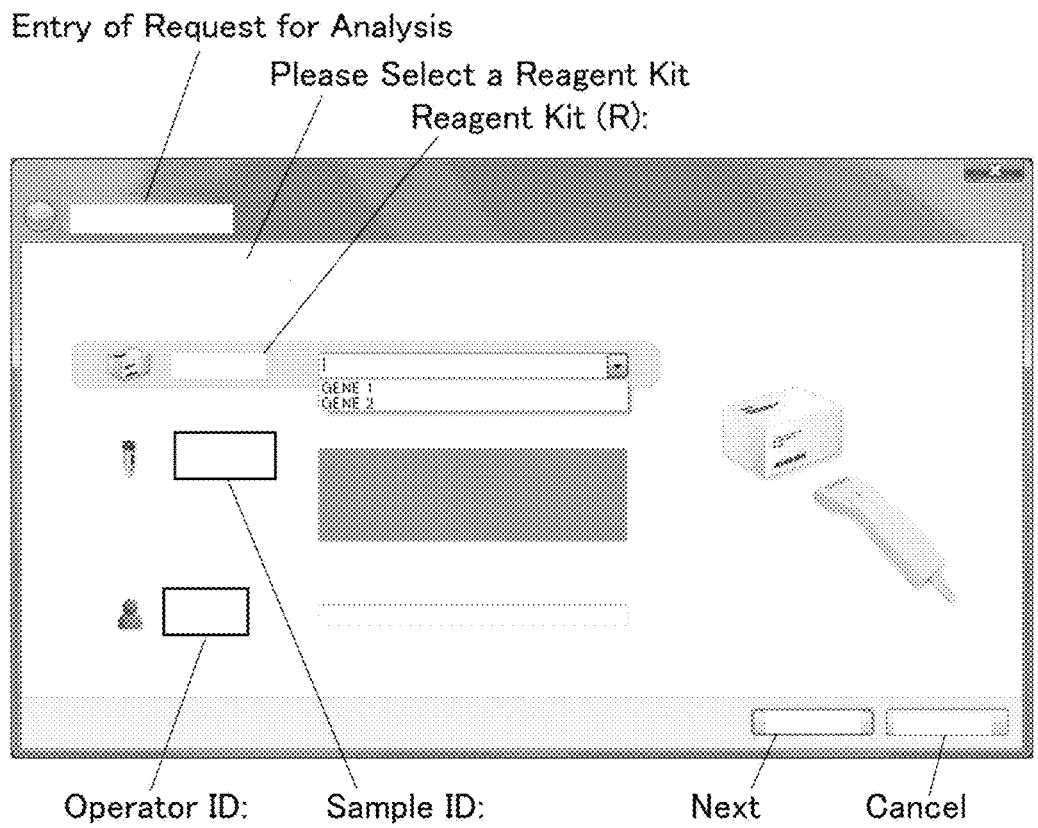
FIG. 3 shows a screen for designating a reagent kit in the example.

The operation starts with the step of inputting items for request for analysis. Specifically, when a screen for "Entry of request for analysis" appears on the display unit 110 as shown in FIG. 3, necessary information is inputted using a keyboard, a bar code reader, or the like of the input unit 106 according to instructions displayed on the screen. In this case, the reagent kit information storing means 104 stores information regarding two reagent kits "GENE 1" and "GENE 2" as the two or more reagent kits, and therefore, the names of these reagent kits are displayed. An operator can input a reagent kit name by designating one of the displayed reagent kits with the use of a keyboard or a mouse of the input unit 106. When the package of a reagent kit to be used has a bar code representing its name, a reagent kit name may be inputted through a bar code reader. Alternatively, a reagent kit name may be inputted as literal information through a keyboard.

Figure 4:
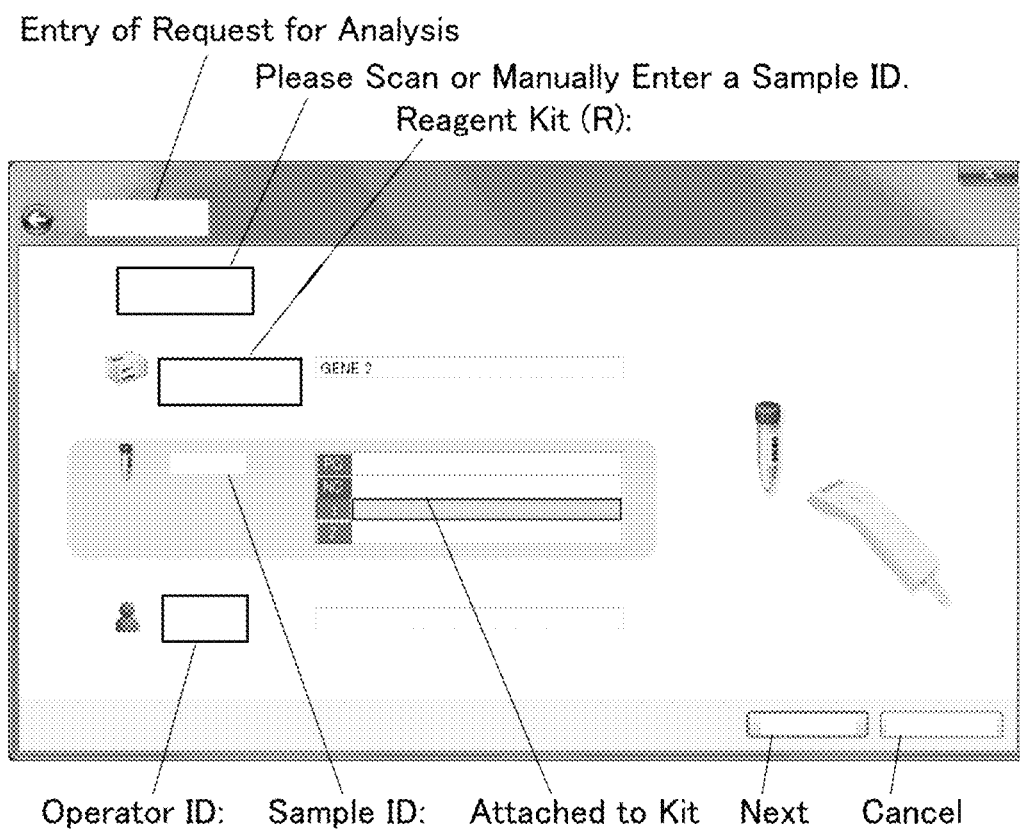
FIG. 4 shows a screen for inputting the number of samples in the example.

When the input of a reagent kit name is finished, the screen displayed on the display unit 110 is changed to a screen for inputting the number of samples as shown in FIG. 4. The inputted reagent kit name is displayed on the top line of the screen. In the case shown in FIG. 4, the inputted reagent kit name is "GENE 2". The next columns on this screen are used to input a sample, and the signs "PC" and "NC" are displayed in advance. The signs "PC" and "NC" refer to a positive control sample and a negative control sample, respectively. In the case shown in FIG. 4, a positive control sample and a negative control sample included in the reagent kit are used.

Below the sign "NC", sample numbers 1 and 2 are assigned to the columns. When sample IDs for identifying individual samples are inputted into these columns, the number of inputted sample IDs is recognized as the number of samples. When a sample container containing a sample has a bar code label representing a sample ID attached thereon, the input of a sample ID can be performed by reading the bar code label with a bar code reader. The input of a sample ID may be performed through a keyboard. In this case, the operator inputs sample IDs in the columns corresponding to sample numbers 1 and 2 so that the regent amount calculating means 108 of the computer 112 recognizes that the number of samples is 2.

Then, an operator ID for identifying an operator is inputted in the lowermost column through a keyboard to finish the input of the number of samples.

Figure 2A:
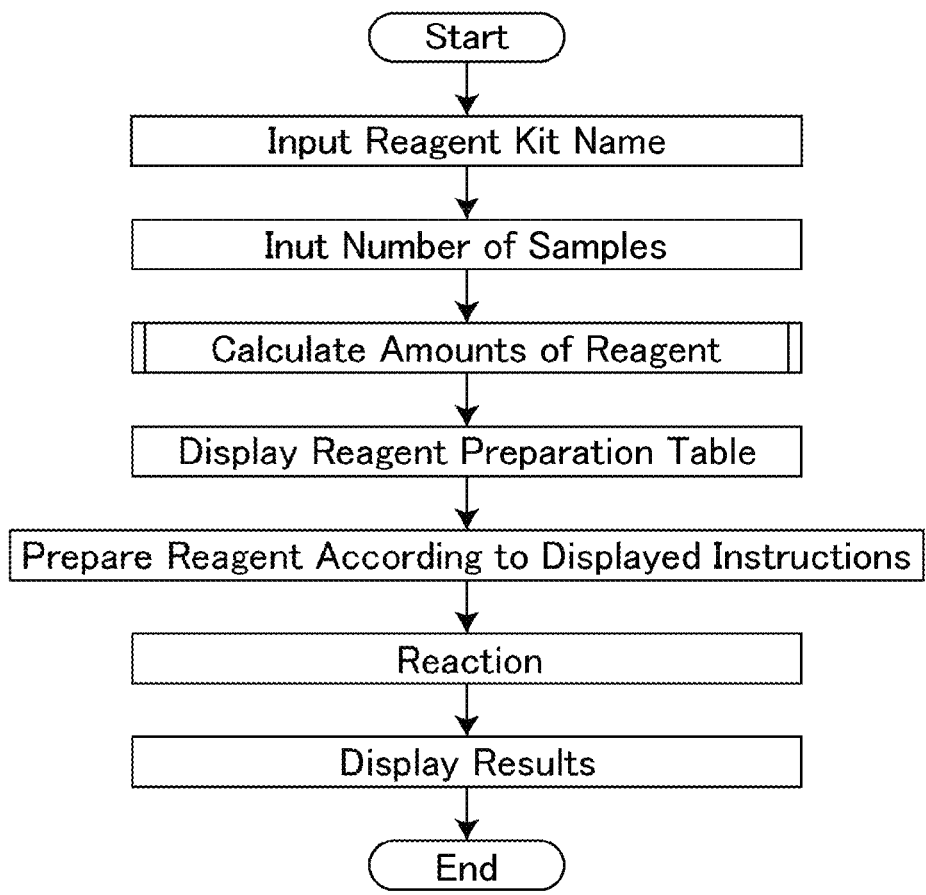
FIG. 2A is a flow chart showing the entire operation of an example of the embodiment.
Figure 2B:
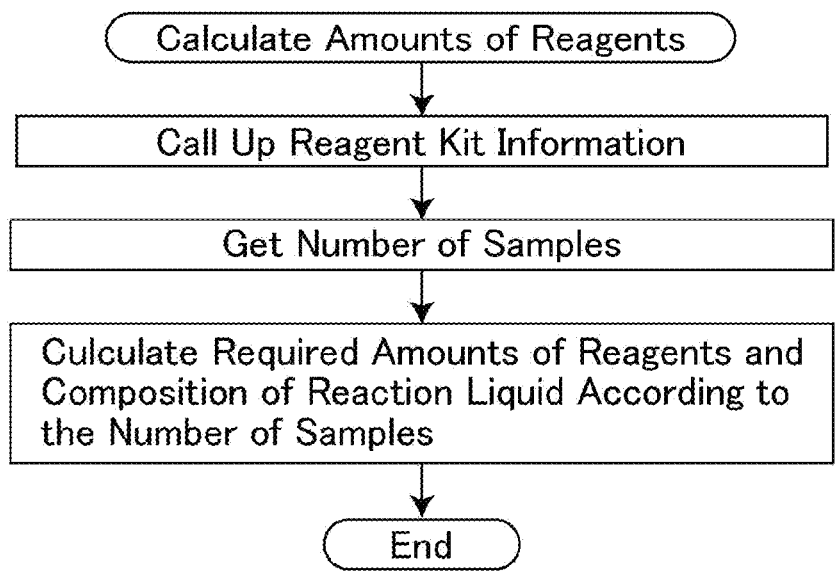
FIG. 2B is a flow chart showing the operation of calculating the amounts of reagents by reagent amount calculating means in the example.

That is everything that the operator needs to do for input operation. When the input of the number of samples is finished, as shown in FIG. 2B, the reagent amount calculating means 108 of the computer 112 calls up, from the reagent kit information storing means 104, the data regarding the reagent kit "GENE 2" inputted through the input unit 6, and calculates the required amounts of reagents included in the reagent kit and the compositions of reaction liquids according to the number of samples "2" inputted through the input unit 106.

Figure 5:
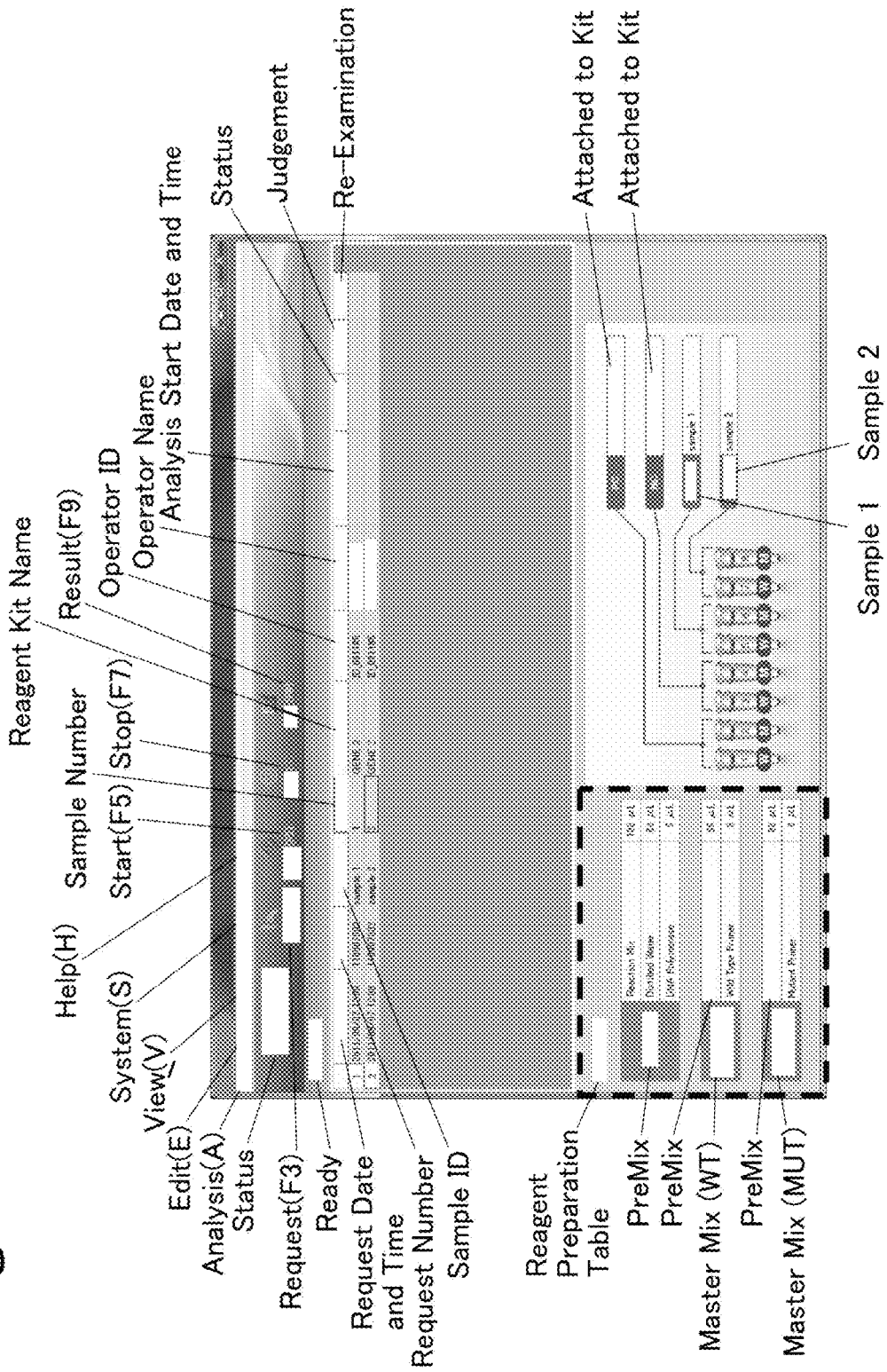
FIG. 5 shows a screen displaying a reagent preparation table in the example.

When the reagent amount calculating means 108 calculates the required amounts of reagents and the compositions of reaction liquids, the screen displayed on the display unit 110 is changed to one shown in FIG. 5. As shown in FIG. 5, requested date and time of reaction liquid preparation, request number, sample ID, sample number, reagent kit name, operator ID, and operator name are displayed on the top line of the screen, and a reagent preparation table is displayed in the lower-left area of the screen surrounded by a bold dotted line.

The uppermost column in the reagent preparation table indicates that a common mixed liquid (Premix) needs to be prepared by adding 88 µL of distilled water to 100 µL of a first reagent "Reaction Mix" included in the reagent kit "GENE 2" and 8 µL of a second reagent "DNA Polymerase" included in the reagent kit "GENE 2". The middle column indicates that a first reaction liquid "Master Mix (WT)" needs to be prepared by adding 8 µL of a third reagent "Wild Type Primer" to 88 µL of the prepared common mixed liquid, and the lowermost column indicates that a second reaction liquid "Master Mix (MUT)" needs to be prepared by adding 8 µL of a fourth reagent "Mutant Primer" to 88 µL of the prepared common mixed liquid.

On the right side of the reagent preparation table, a procedure for preparing reaction solutions is displayed. The procedure indicates that eight tubes or an 8-strip tube in which individual tubes are linked together need/needs to be prepared to dispense a positive control sample attached to the reagent kit "GENE 2", a negative control sample attached to the reagent kit "GENE 2", a first sample, and a second sample into the tubes 1 and 2, the tubes 3 and 4, the tubes 5 and 6, and the tubes 7 and 8, respectively. Further, the sign "W" or "M" attached to each of the tubes indicates that the first reaction liquid "Master Mix (WT)" or the second reaction liquid "Master Mix (MUT)" prepared according to the reagent preparation table needs to be dispensed into the tube.

The operator prepares the reaction liquids according to the reagent preparation table displayed on this screen, and then dispenses the control sample or the sample and the prepared reaction liquid into the tubes according to instructions displayed together with the arranged tubes to prepare reaction solutions.

When the operator sets the tubes containing the prepared reaction solution in the analyzer 102 to start analysis, analysis start date and time and analysis progress status are displayed in the upper column of the display screen shown in FIG. 5. When the analysis is finished, the result of judgment on the sample is displayed, and the necessity of re-examination is also displayed based on judgment as to whether the analytical value of the sample is within a normal range.

The displaying of analysis start date and time and status and the judgment on the analytical result are functions performed by the data processing computer of the analyzer 102. When the reagent preparation supporting device according to the present invention is implemented using the data processing computer of the analyzer 102 as the computer 112, the display for the analyzer 102 and the display by the reagent preparation supporting device of this example are displayed on the same display unit 110, and therefore, the operator can see them at the same time.

When the analysis is finished, information displayed on the screen shown in FIG. 5 is stored in the reaction liquid information storing means 114, which makes it possible to call up the information at any time to display the information on the display unit 110.

As another example, the reagent preparation supporting device of this example will be described with reference to a case where a rack for placing tubes for reagent preparation is provided. Such a rack is provided for each reagent kit. Two or more racks different in the number of samples that can be prepared may be provided for each reagent kit. However, from the viewpoint of rack management, one kind of rack formed so that up to a maximum possible number of samples can be prepared is preferably provided for each reagent kit.

Figure 6A:
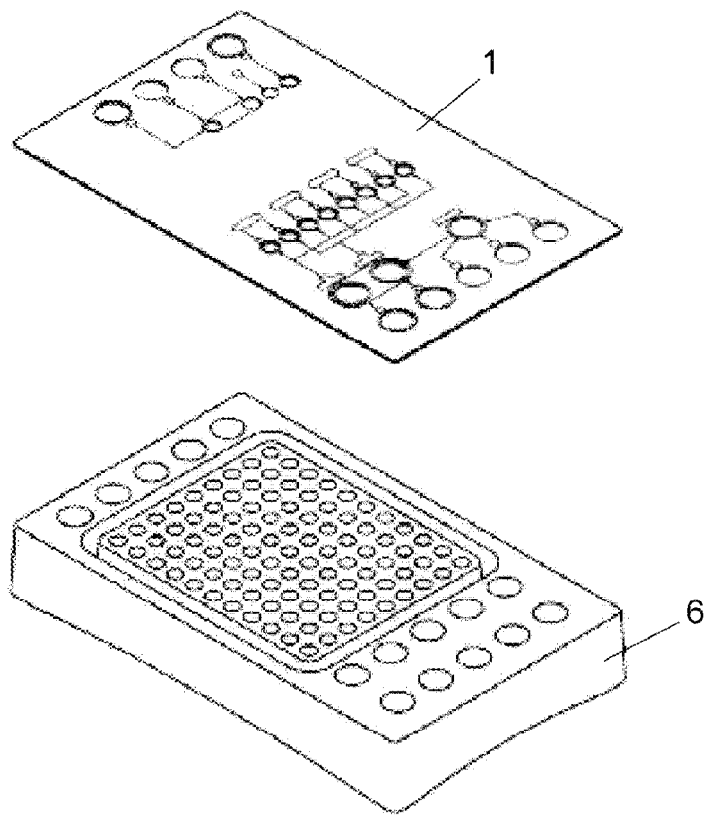
FIGS. 6A and 6B are an exploded perspective view and a perspective view, respectively, of one example of a rack that is sometimes provided together with a reagent kit.
Figure 6B:
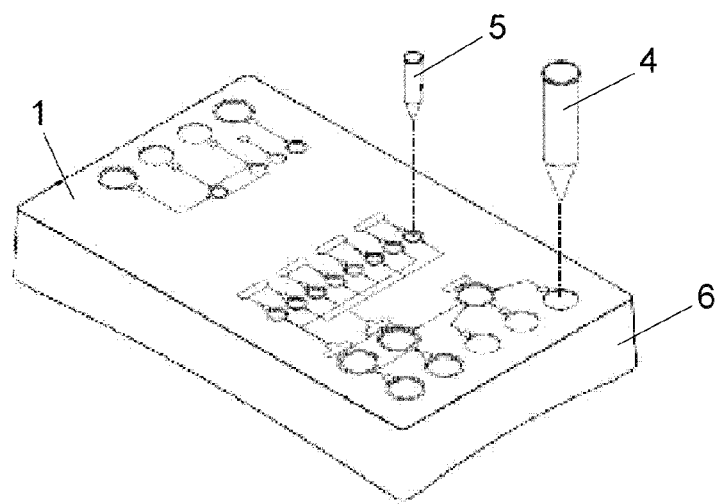

One example of such a rack is shown in FIGS. 6A and 6B. As shown in FIG. 6A, the rack is a combination of a tube holding plate 1 and a commercially-available tube rack 6. The tube holding plate 1 is formed so that its holes correspond to the holes of the tube rack 6. Here, the tube holding plate 1 shown in FIG. 6A is one formed so that reagents can be prepared for up to 2 samples to simplify the drawings. The tube holding plate 1 for two samples can be used to prepare reagents for one or two samples. Here, a description will be made with reference to a case where reagents are prepared for 2 samples. As shown in FIG. 6B, the tube holding plate 1 is superposed on the tube rack 6 so that the positions of their holes coincide with each other.

Figure 7:
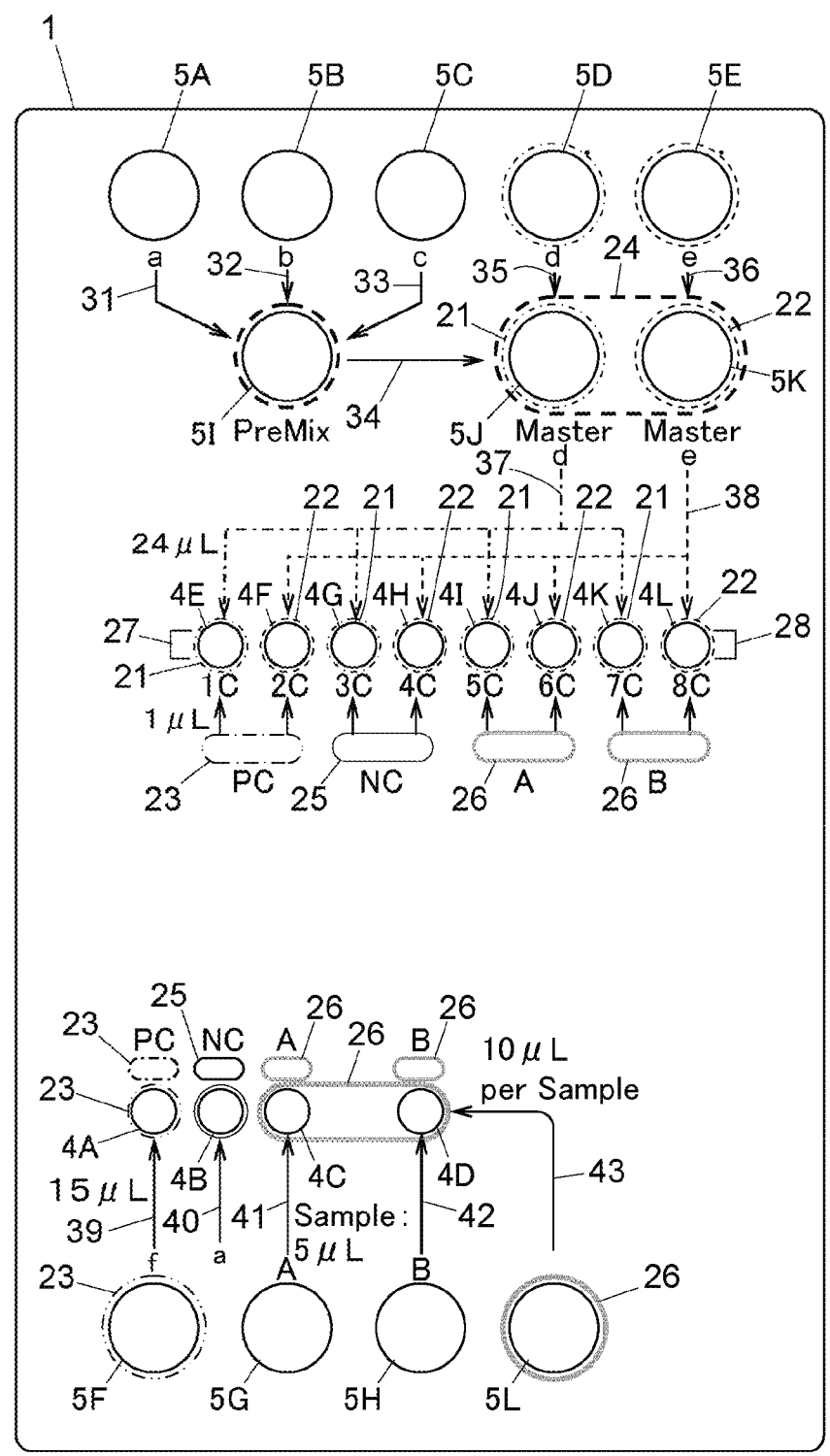
FIG. 7 is a plan view of one example of a plate of the rack.

As shown in FIG. 7, the tube holding plate 1 is a rectangular plate 1 having a plurality of circular punched holes into which tubes are to be inserted. Specifically, 12 punched holes 4A to 4L having a smaller diameter and 12 punched holes 5A to 5L having a larger diameter are provided.

Around the holes, figures different in color, line type, or shape that identify corresponding reagent types or tubes or characters that identify corresponding reagent types or tubes are displayed. In addition, a procedure for preparing reagents is visually displayed by appropriately arranging the holes and drawing arrows between the holes. It is to be noted that the characters that identify corresponding reagent types or tubes include symbols.

When the rack for placing tubes for reagent preparation is provided, the reagent preparation supporting device of this example further includes rack screen storing means 120 and display control means 122. The rack screen storing means 120 stores the image data of a rack screen showing the positions of holes for placing tubes for reagent preparation in the tube holding plate 1 of the rack. The display control means 122 allows the display unit 110 to display the rack screen stored in the rack screen storing means 120, to show, on the displayed rack screen, the positions of holes for placing tubes for reagent preparation required to prepare the reagents according to the reagent preparation table, and to also display a procedure for preparing the reagents and the injection amounts of the reagents based on the reagent preparation table. The injection amounts of the reagents are appropriately displayed, for example, in or around the holes for placing tubes for reagent preparation.

A rack screen 1*a* displayed on the display unit 110 so as to correspond to the rack shown in FIGS. 6 and 7 corresponds to the tube holding plate 1, and the positions of holes for placing tubes for reagent preparation on the rack screen correspond to the positions of holes of the tube holding plate 1.

Figure 8:
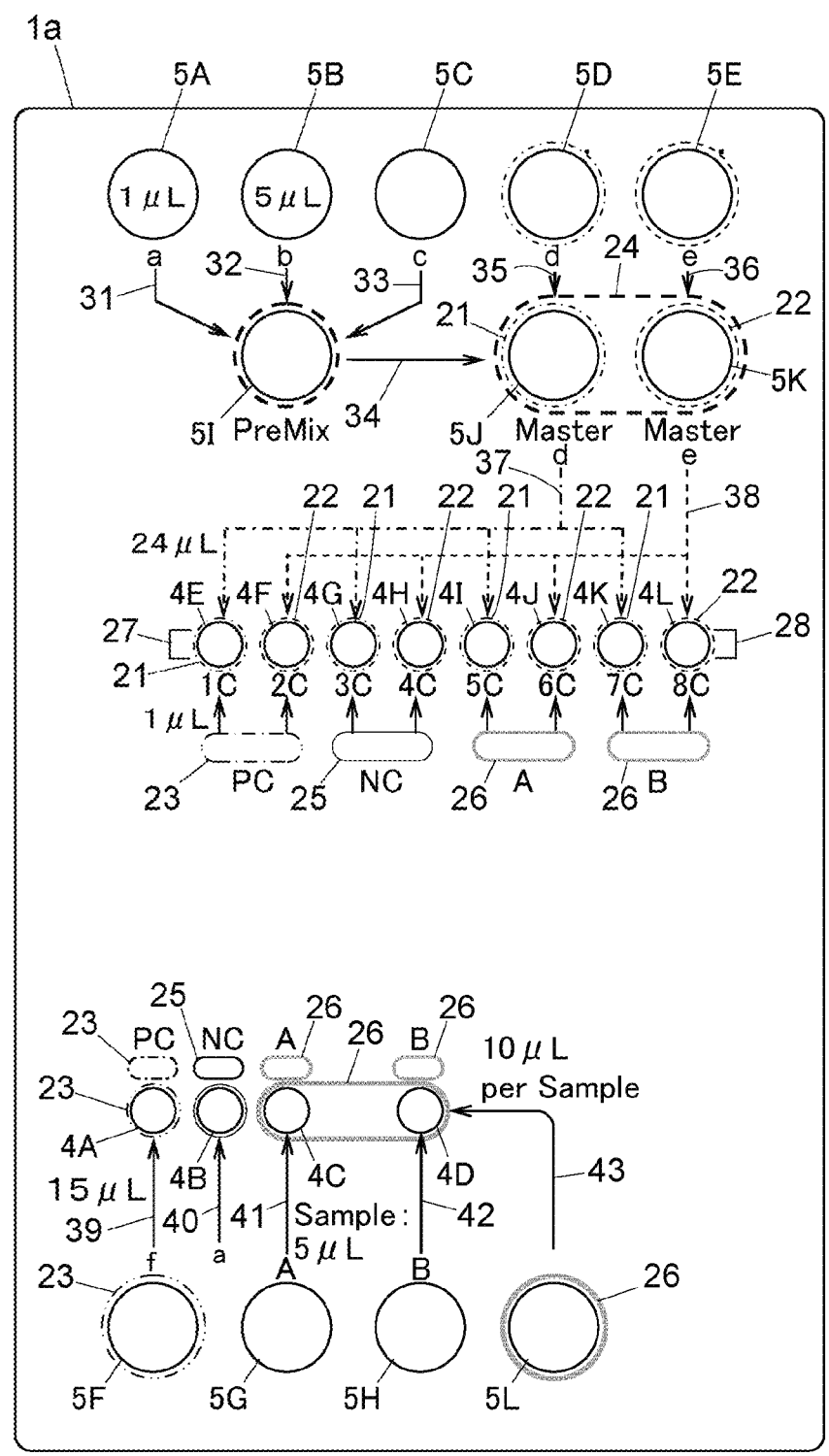
FIG. 8 shows a rack screen displayed on a display unit, which corresponds to the plate of the rack.

FIG. 8 shows the rack screen 1*a* on which the positions of holes for placing tubes for reagent preparation required to prepare the reagents according to the reagent preparation table for preparing the reagents for two samples are shown and a procedure for preparing the reagents and the injection amounts of the reagents based on the reagent preparation table are also displayed.

In the first line, the holes 5A, 5B, and 5C are marked with reagent codes a, b, and c, respectively, and the holes 5D and 5E are marked with reagent codes d and e, respectively. Further, the holes 5D and 5E are surrounded by colored marks 21 and 22, respectively. Around each of the holes 5A to 5E, the injection amount of the reagent is also displayed. For the sake of simplifying the drawing in FIG. 8, the injection amounts of the reagents are displayed only around the holes 5A and 5B, but the injection amounts of the reagents are also displayed around the other holes 5C to 5E.

In the second line, the hole 5I is surrounded by a colored mark 24, and the caption "PreMix" is displayed near the hole 5I. Further, the hole 5J is surrounded by the colored mark 21, the caption "Master-d" is displayed near the hole 5J, the hole 5K is surrounded by the colored mark 22, and the caption "Master-e" is displayed near the hole 5K. Further, the holes 5J and 5K are surrounded together by the colored mark 24. The colored mark refers to a figure that is displayed near the periphery of hole of the tube holding plate and is color-coded according to the type of reagent, tube, or sample.

In the third line, the holes 4E, 4G, 4I, and 4K are surrounded by the colored mark 21 and marked with symbols 1*c*, 3*c*, 5*c*, and 7*c*, respectively. The holes 4F, 4H, 4J, and 4L are surrounded by the colored mark 22 and marked with symbols 2*c*, 4*c*, 6*c*, and 8*c*, respectively. Further, the symbols 1*c* and 2*c* are marked with a common symbol PC, the symbols 3*c* and 4*c* are marked with a common symbol NC, the symbols 5*c* and 6*c* are marked with a common symbol A, and the symbols 7*c* and 8*c* are marked with a common symbol B. In addition, the symbol PC is marked with a colored mark 23, the symbol NC is marked with a colored mark 25, and the symbols A and B are each marked with a colored mark 26.

In the fourth line, the hole 4A is surrounded by the colored mark 23 and marked with a symbol PC marked with the same colored mark 23. The hole 4B is surrounded by the colored mark 25 and marked with a symbol NC marked with the same colored mark 25. The holes 4C and 4D are surrounded together by the colored mark 26 and marked with symbols A and B marked with the same colored mark 26, respectively.

In the fifth line, the hole 5F is surrounded by the colored mark 23 and marked with a reagent code f. The holes 5G and 5H are marked with sample codes A and B, respectively, and the hole 5L is surrounded by the colored mark 26 and marked with a reagent code g.

Further, in the spaces between the holes, arrows indicating an operating procedure, injection amounts of the reagents, and precautions are displayed.

The operator prepares the reagents according to instructions on the rack screen 1*a* displayed on the display unit 110. The details shall be further described.

Empty tubes (hereinafter, tube numbers are the same as hole numbers) are inserted into their designated holes (marked with 4 and 5 by way of example in the drawing) having the size matches that of the tubes. Then, the reagents are prepared according to the arrows.

First, predetermined amounts of reagents a, b, c, d, e, f, and g are injected into the tubes 5A, 5B, 5C, 5D, and 5E in the first line and the tubes 5F and 5L in the fifth line, respectively, a predetermined amount of a sample A is injected into the tube 5G, and a predetermined amount of a sample B is injected into the tube 5H.

Then, the reagents a, b, and c in the tubes 5A, 5B, and 5C in the first line are mixed in the tube 5I in the second line according to the arrows 31, 32, and 33. Further, a predetermined amount of the mixed liquid in the tube 5I is dispensed into each of the tubes 5J and 5K according to the arrow 34.

Then, a predetermined amount of the reagent d in the tube 5D in the first line is mixed with the mixed liquid in the tube 5J in the second line according to the arrow 35, and then the mixed liquid in the tube 5J is further dispensed into the tubes 4E, 4G, 4I, and 4K in the third line in an amount of 24 μL per tube according to the arrow 37.

Similarly, a predetermined amount of the reagent e in the tube 5E in the first line is mixed with the mixed liquid in the tube 5K in the second line according to the arrow 36, and then the mixed liquid in the tube 5K is further dispensed into the tubes 4F, 4H, 4J, and 4L in the third line in an amount of 24 μL per tube according to the arrow 38. Also in the plate 1 of the rack, holes for the tubes 4E, 4G, 4I, and 4K are surrounded by the colored mark 21 and holes for the tubes 4F, 4H, 4J, and 4L are surrounded by the colored mark 22, which makes it possible for the operator to differentiate them at a glance and therefore to avoid the error of dispensing. This is the end of the preparation of reaction liquids.

Then, 15 μL of the reagent f in the tube 5F in the fifth line is injected into the tube 4A in the fourth line according to the arrow 39, and a predetermined amount of the reagent a in the tube 5A in the first line is injected into the tube 4B in the fourth line according to the arrow 40. Then, the reagent g in the tube 5L in the fifth line is dispensed into the tubes 4C and 4D in an amount of 10 μL per tube according to the arrow 43. 5 μL of the sample A in the tube 5G is then mixed with the reagent g in the tube 4C according to the arrow 41, and 5 μL of the sample B in the tube 5H is mixed with the reagent g in the tube 4D according to the arrow 42.

The reagents injected into the tubes 4A and 4B in the fourth line and the samples mixed with the reagent in the tubes 4C and 4D in the fourth line are subjected to heat treatment. Then, the reagent PC in the tube 4A, the reagent NC in the tube 4B, the sample A in the tube 4C, and the sample B in the tube 4D are injected into the tubes 4E and 4F, the tubes 4G and 4H, the tubes 4I and 4J, and the tubes 4K and 4L, respectively, in an amount of 1 µL per tube according to the arrow 44 in the third line to perform analysis.

It is further preferred that the display control means 122 in the computer 112 is connected with an external signal input device 124, such as a switch, for inputting an external signal relating to a reagent preparation operation. The external signal relating to a reagent preparation operation is a signal inputted each time one step of reagent preparation is finished, and is generally inputted by the operator. The operator has no hands free due to reagent preparation, and therefore, the external signal input device 124 is preferably a foot switch through which a signal can be inputted by pressing with a foot. Of course, another input means may be used. When receiving the external signal relating to a reagent preparation operation, the display control means 122 changes the display on the rack screen 1*a* displayed on the display unit 110 according to the reagent preparation procedure by, for example, heightening the color of the tube(s) in operation, lightening the color of the treated tube(s), or lighting up the periphery of the tube(s) in operation or the arrow(s) pointing to the tube(s) in operation.

An example of a reagent preparation supporting program for allowing a computer or data processing computer as a control unit of the analyzer 102 or a general-purpose personal computer utilized as the computer 112 to implement the function of the reagent preparation supporting device is a program developed by software for implementing the function of the reagent preparation supporting device of the above-described example.

DESCRIPTION OF REFERENCE SIGNS

1: Plate of rack
6, 50: Rack
1*a*: Displayed rack screen
102: Analyzer
104: Reagent kit information storing means
106: Input unit
108: Reagent amount calculating means
110: Display unit
112: Computer
120: Rack screen storing means
124: Switch

The invention claimed is:

1. A reagent preparation supporting device comprising:
a storage unit configured to store, as data, amounts of each reagent required for analysis of one sample using a reagent kit for sample analysis, composition of a plurality of kinds of reaction liquids to be prepared for reacting sample and the number of reactions to be performed at an analysis of samples, wherein the reagent kit includes a plurality of reagents, and wherein the plurality of kinds of reaction liquids are composed of at least one different reagent of the reagent kit and a common mixed liquid which is composed of some of the reagents of the reagent kit;
an input unit that performs input of the number of samples to be analyzed;
a reagent amount calculator, that is implemented by software on a computer and that is configured to call up the data regarding the reagent kit, the composition of the plurality of kinds of reaction liquids and the number of reactions to be performed at an analysis of samples from the storage unit, and to calculate the number of reactions to be performed at an analysis of the samples, a composition of the common mixed liquid required to prepare the reaction liquids for reacting the samples and amounts of the common mixed liquid and reagents required to compose the reaction liquid according to the number of samples inputted through the input unit and the number of reactions to be performed at an analysis of sample stored by the storage unit; and
a display unit that displays, as a reagent preparation table, the composition of the common mixed liquid and the reaction liquids, and the amounts of the common mixed liquid and the reagents required to compose the reaction liquid based on results calculated by the reagent amount calculator.

2. The reagent preparation supporting device according to claim 1, wherein the storage unit stores data regarding two or more kinds of reagent kits,
the input unit is configured to designate any one of the two or more kinds of reagent kits data of which is stored in the storage unit,
the reagent amount calculator configured to call up from the storage unit, the data regarding the reagent kit designated through the input unit, and to calculate a composition of the reaction liquid for reacting the samples and amounts of the reagents required to compose the reaction liquid.

3. The reagent preparation supporting device according to claim 2, wherein the storage unit is configured to be recordable so that data regarding a new reagent kit can be added thereto.

4. The reagent preparation supporting device according to claim 1, comprising reaction liquid information storing means that is capable of storing the results calculated by the reagent amount calculator and calling up the results at any time to display the results on the display unit.

5. The reagent preparation supporting device according claim 1, wherein the display unit also displays tubes for reagent preparation and reagents, a sample, or a reaction liquid to be dispensed into the individual tubes.

6. The reagent preparation supporting device according to claim 1, further comprising, when a rack for placing tubes for reagent preparation is provided, rack screen storing means that stores image data of a rack screen showing positions of holes for placing tubes for reagent preparation in the rack, and
display control means that allows the display unit to display the rack screen stored in the rack screen storing means, to show, on the displayed rack screen, positions of holes for placing tubes for reagent preparation required to prepare the reagents according to the reagent preparation table, and to also display a procedure for preparing the reagents based on the reagent preparation table.

7. The reagent preparation supporting device according claim 6, wherein the display control means allows the display unit to also display injection amounts of the reagents prepared based on the reagent preparation table.

8. The reagent preparation supporting device according claim 6, wherein when receiving an external signal relating to a reagent preparation operation, the display control means changes display on the rack screen showing positions of holes for placing tubes for reagent preparation and displayed on the display unit according to the reagent preparation procedure.

* * * * *